United States Patent [19]

Kinney et al.

[11] 4,262,673

[45] Apr. 21, 1981

[54] FLUID TIGHT COUPLING FOR ELECTRODE LEAD

[75] Inventors: Philip C. Kinney, Pittsburgh; Marlin S. Heilman, Gibsonia; Albert J. Hrubes, Mars, all of Pa.

[73] Assignee: Mieczyslaw Mirowski, Owings Mills, Md.

[21] Appl. No.: 83,967

[22] Filed: Oct. 11, 1979

[51] Int. Cl.³ ............................................. A61N 1/00
[52] U.S. Cl. ............................................... 128/419 P
[58] Field of Search ........ 128/419 D, 419 P, 419 PG, 128/419 PS

[56] References Cited

U.S. PATENT DOCUMENTS

| | | | |
|---|---|---|---|
| 4,072,154 | 2/1978 | Anderson et al. | 128/419 P |
| 4,141,752 | 2/1979 | Shipke | 128/419 P |

*Primary Examiner*—William E. Kamm
*Attorney, Agent, or Firm*—Fleit & Jacobson

[57] ABSTRACT

A fluid-tight electrical coupling for a medical device fully implantable in the body of a recipient, such as an implantable defibrillator, is disclosed. The fluid-tight coupling is mounted on a hermetically sealed casing. The coupling comprises a housing having receptacles for receiving an electrical conductor plug. Terminal blocks are provided within the housing and define a pin opening for receiving the pins of the electrical conductor plug. The terminal block is electrically connected to the exterior of the housing. The terminal block also includes a cylindrically shaped boss extending from a face of the terminal block. The boss is externally and internally threaded for receiving a sealing cap and a retaining member respectively. The retaining member comprises a hexagonal socket head set screw. The sealing cap seals off the interior of the housing. The sealing cap is secured to the terminal block to seal off the housing opening by means of a screwdriver that is adapted to retain the sealing cap thereto. Also disclosed is a maximum torque wrench to prevent overtightening of the set screw.

16 Claims, 6 Drawing Figures

FLUID TIGHT COUPLING FOR ELECTRODE LEAD

BACKGROUND OF THE INVENTION

This invention relates to a fluid-tight electrical coupling system for implantable medical devices, such as implantable defibrillators.

Great strides are presently being made to develop an automatic, fully implantable defibrillator. See, for example, U.S. Pat. Nos. Re. 27,652 and Re. 27,757, where the first concept of the automatic implantable ventricular defibrllator is described. Recent advances have also been made in enhancing the reliability of fibrillation detectors. In this latter regard, see co-pending U.S. patent applications Ser. Nos. 878,005 and 878,006, each filed on Feb. 15, 1978 and now U.S. Pat. Nos. 4,202,340 and 4,184,493 respectively. Furthermore, as outlined in co-pending U.S. Pat. application Ser. No. 801,300, filed on May 27, 1977, and now U.S. Pat. No. 4,164,946, steps have been taken to improve the reliability of the implanted defibrillator by the provision of circuitry which interrogates the implanted electronics to verify proper operation before a defibrillating shock is delivered.

In co-pending U.S. Pat. application Ser. No. 53,797, filed on July 2, 1979, entitled "Implantable Defibrillator Package" incorporated herein by reference, an implantable defibrillator package is disclosed having an implantable casing, or housing, and a lid portion hermetically sealed to the casing to form a hermetic seal. An epoxy housing is provided on the lid portion for receiving electrode leads having plugs, the electrodes leads also implantable in the body of a recipient. Terminal blocks within the epoxy housing receive portions of the plugs, and electrical conductors interconnect the terminal blocks with feed-through electrical terminal pins extending into the epoxy housing, and through the lid portion, for electrical communication with circuitry disposed in the casing.

It is highly desirable that the plugs be physically secure within the terminal block, and yet be fully explantable for replacement. Moreover, fluid seepage into the terminal block area must be prevented to ensure corrosion-free contact between the terminal block and the plug, thus assuring electrical integrity of the connection and easy removal of the plug from the terminal block for replacement.

It is thus essential that any openings in the epoxy housing be sealed to prevent leakage into the housing interior. Sealing elements are known which included caps which either snap into the device to be sealed or have a bayonet-type connection.

The present invention is directed toward filling the needs expressed above.

SUMMARY OF THE INVENTION

The subject invention relates to a fluid-tight electrical coupling for implantable medical devices. The fluid-tight coupling is mounted on an implantable casing to couple one or more electrical conductor plugs with electrical circuitry disposed within the casing. The fluid-tight coupling comprises a housing mounted on the casing having terminal blocks for receiving pin elements of electrical conductor plugs and for receiving a retainer member for retaining the pin elements in the terminal block. The retainer member, preferably a set screw, is inserted through an opening in the housing. A maximum torque wrench is provided to removably secure the retainer member in the terminal block. The opening through which the retainer member passes is sealed by an internally threaded sealing cap, in threaded engagement with the terminal block, to provide a seal between the housing and the housing interior. A screwdriver is provided to engage and retain the sealing cap for delivery to the housing opening.

It is thus an object of the present invention to provide an electrical coupling device, preferably implantable in the body of a recipient, for coupling an electrical conductor plug with an electrical conductor and to isolate the connection from the outside environment. Such a coupling device avoids fluid seepage, which may impair the conductivity of the connection, and avoids corrosion, thus ensuring easy removability of the plug from the terminal block.

It is another object of the present invention to provide a secure connection between the terminal block and the plug so that vibration and shock do not cause accidental disconnection. A separate retaining member is provided to be inserted through the housing, and through the terminal block, into engagement with the plug to retain the plug in the terminal block.

It is a further object of the present invention to provide a sealing cap for securely, yet removably, sealing a housing opening. It is thus an object to provide a driving member, such as a screwdriver, associated with the sealing cap for retaining and inserting the cap into the housing opening in a simple manner, using minimum steps. Preferably, the sealing cap must be delivered and secured with only a single hand, which is preferable in a surgical arena.

Another object of the present invention is to provide an electrical coupling that can safely and quickly be decoupled thus permitting unplugging of the plug after long periods of use in the body of the recipient. It is thus an object of the invention to ensure that the retaining member, preferably a set screw, not be overtightened or overtorqued during assembly. This facilitates removal of the retaining member, should such removal be necessary, and avoids deformation of the plug member. Thus, a maximum torque wrench is provided to prevent overtorquing.

Other objects and advantages of this invention will further become apparent when reference is made to the following description and to the accompanying drawings.

DETAILED DESCRIPTION OF THE DRAWINGS

Figure 1:
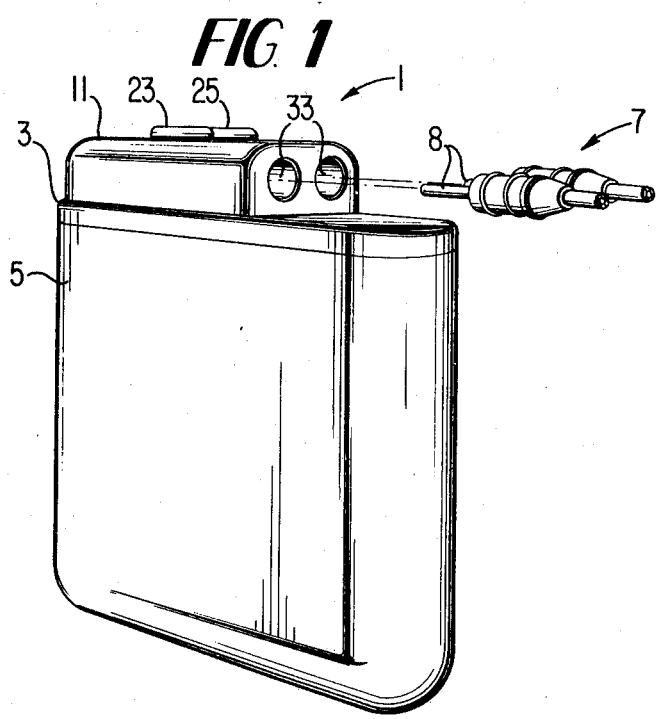
FIG. 1 is a perspective of the assembled housing.
Figure 4:
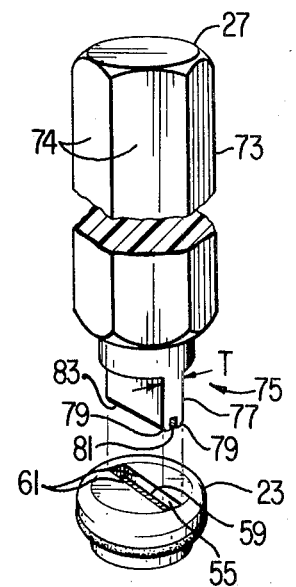
FIG. 4 is a perspective view of the screwdriver and sealing cap.
Figure 2:
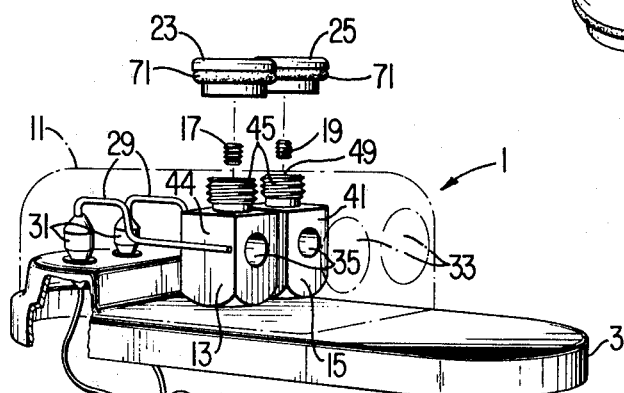
FIG. 2 is an exploded perspective of the lid portion of the housing with the electrical coupling mounted thereon.
Figure 2:
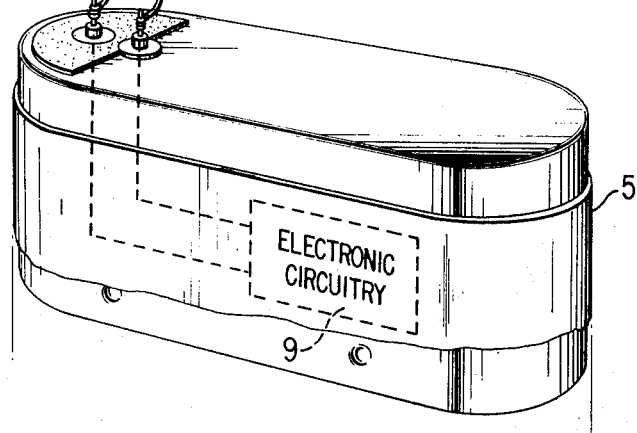

A preferred embodiment of the present invention includes an electrical coupling 1 secured to a lid 3 of a casing 5, for electrical coupling of electrical conductor plugs 7 with electronic circuitry 9 disposed within the casing 5. The casing 5 houses defibrillator circuitry, as described in co-pending U.S. Pat. application Ser. No. 53,797, filed on July 2, 1979, entitled "Implantable Defibrillator Package", incorporated herein by reference.

The coupling 1 comprises a housing 11 supporting a pair of terminal blocks 13, 15. Plugs 7 are insertable into the housing 11, and include electrically conducting pins 8 insertable into the terminal blocks 13, 15 and secured therewithin by retaining members 17, 19. The retaining members 17, 19 are insertable through the housing and threaded into the terminal blocks by a maximum torque wrench 21. Sealing caps 23, 25 are threaded to the terminal blocks to seal the housing opening 37. A driving member 27 is provided to retain the sealing caps 23, 25 for delivery to the housing 11 and for imparting rotary motion to the sealing caps 23, 25 for connection with the terminal blocks 13, 15.

It should be recognized that the electrical coupling 1 of the present invention has utility in other environments, particularly in other implantable medical devices, such as pacemakers and the like.

The housing, or header, 11 comprises a unitary element of electrical insulating material. Preferably, the housing 11 is a molded plastic material, such as epoxy. The housing 11 is substantially solid, except for those spaces that receive the internal components. Preferably, the housing can be molded integral with the lid 3 with the terminal blocks 13, 15, electrical conducting wires 29, and insulators 31, disposed within the mold.

Figure 3:
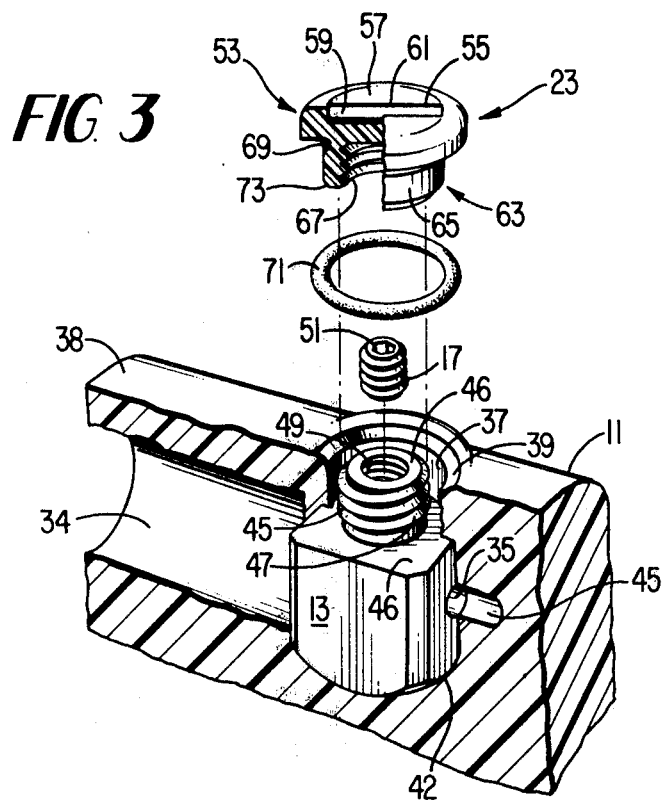
FIG. 3 is a sectional view of part of the electrical coupling.
Figure 5:
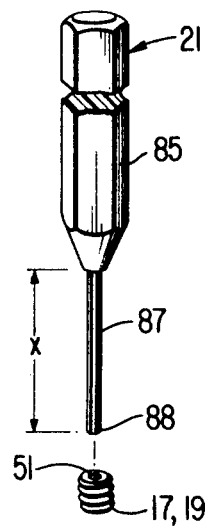
FIG. 5 is a perspective view of the maximum torque wrench and set screw.

Housing 11 defines a pair of receptacles 33 for receiving plugs 7. The receptacles are cylindrically shaped bores 34 concentric with pin openings 35 of the terminal blocks 13, 15. The housing 11 further defines a pair of housing openings 37 (only one shown, in FIG. 3), also in the form of cylindrical bores, extending from the top surface 38 of the housing, substantially perpendicular to receptacle bores 33 and pin openings 35. Annular chamfers 39 are defined by the openings and mate with O-rings 71 on the sealing caps 23, 25 to be described further below.

The terminal blocks 13, 15 are encased within housing 11, the latter being preferably molded about the terminal blocks. The terminal blocks 13, 15 are made of electrically conductive material, such as a conductive metal. Each terminal block is identical and for purposes of discussion, only terminal block 13 will be described in detail.

Terminal block 13 comprises a substantially rectangular prism shaped block with rounded, or beveled, edges. A cylindrically threaded boss 45 extends from the top surface 46 of the prism into the housing opening 37, described further below. A pin opening 35 is defined by the terminal block and extends entirely therethrough. The pin opening 35 is located substantially at the center of the terminal block face 41 and is adapted to receive an electrical conducting pin 8 of the electrical conducting plug 7. The pin opening 35 is preferably drilled and reamed after assembly in the housing 11. Thus, the pin opening 35 is concentric with the receptable bore 34 of the housing 11. In drilling the pin opening 35, an opening 45 in the solid plastic housing 11 is likewise drilled to accommodate the pin 8 that extends entirely through front block face 41 and rear block face 42 of the terminal block 13.

Electrically conducting wires 29, preferably of platinum, are fixed in electrical contact with side faces 44 of the terminal blocks 13, 15. The wires 29 extend through housing 11 and through insulators 31, to the housing exterior. The feed through assembly of wires 29 are described in the co-pending application Ser. No. 53,797 referred to above.

The substantially cylindrical boss 45 extends centrally from the top surface 46 of the prism shaped portion of the terminal block 13. The boss 45 is substantially perpendicular to the pin opening 35. The boss 45 is externally threaded at 47 for threaded engagement with a sealing cap 23. A retaining member opening in the form of a threaded bore 49 extends through the terminal block boss 45 and opens in the pin opening 35. The threaded bore 49 is adapted to receive the retaining member, such as a set screw 17. The threaded bore 49 is substantially perpendicular to the pin opening 35.

The threaded boss 45 extends centrally within the housing opening 37. Preferably, the length of boss 45 is such that its distal end 46 is substantially flush with the top face 38 of the housing 11.

The retaining members are each preferably hexagon socket head set screws 17, 19, as are well known in the art. The set screws measure 0.050 inches across opposite flats. The hexagon socket portion 51 is adapted to receive a corresponding hexagon shaped keyed portion of a maximum torque wrench 21. The set screws 17 and 19 are screwed into the threaded bore 49 and are adapted to engage and secure the pin 8 of the electrical conductor plug 7. It is essential that the set screws not be overtightened, or overtorqued, to ensure their easy removal from the bore 49, thus permitting withdrawal of the conductor plug 7. Although a hexagon socket head is disclosed, it should be appreciated that other shapes can be provided, provided that the corresponding maximum torque wrench 21 is of complementary shape to mate therewith.

Sealing caps 23, 25 serve to seal the housing opening 37 from the environment surrounding the housing. Sealing caps 23, 25 are identical and only one need be described.

Sealing cap 23 is a unitary plastic element, preferably made of Delrin. The head portion 53 is circular in cross-section, having a diameter greater than the diameter of the housing opening 37. Head portion 53 is preferably a round head or pan head configuration.

A notch 55 is provided in the face 57 of the head portion 53. Preferably, the notch 55 is rectangularly shaped in plan view; the lateral faces 59 of the notch 55 are of a transverse length less than the diameter of the head. Sharply defined transverse edges 61 define biasing surfaces for biasing the driving member blade accommodated within the notch in a manner to be described below.

Integral with the head portion 53 is a neck portion 63 of substantially cylindrical shape and having an outside diameter less than the outside diameter of the head portion. Neck portion 63 is substantially perpendicular to the head portion. The neck portion 63 has an external cylindrical surface 65 and an internal surface 67. The external surface 65 extends from the head 53. An annular chamfer 69 is disposed about the neck 63 adjacent the head portion 53. The annular chamfer defines a surface to receive an O-ring 71, preferably made of Silastic material. The O-ring 71 is frictionally fit in the chamfer 69 and acts as a sealing element in a manner to be described below.

The internal surface 67 is threaded for threaded, removable engagement with the threaded surface 47 of the boss 45. The length of the neck portion 63 of the cap 23 is slightly less than the length of the boss 45 so that the distal end 73 of the neck portion 63 does not contact the top surface 46 of the terminal block 13.

When the sealing cap 23, with the Silastic O-ring 71 frictionally and tightly seated in the annular chamfer 69, is screwed onto the boss 45, the O-ring 71 abuts, and is compressed by, the annular chamfer 39 defined by the housing 11. This provides a fluid-tight seal, thus preventing fluid from seeping past the cap 23 and into the housing opening 37, past the set screw 17, and in contact with the connection between the pin 8 and the terminal block 13. Moreover, the internally threaded neck 67, in engagement with the external threaded boss 45, also assists in ensuring that fluid does not leak into the terminal connection.

When the coupling 1 is part of an implantable medical device, the sealing caps 23, 25 will be connected with the terminal block 13 during a surgical procedure. Likewise, when the plug 7 is explanted, the sealing caps 23, 25 must be removed during a surgical procedure. Thus, the sealing caps must be transportable to and from the housing 11 in a safe and secure manner, and with minimum manual effort; preferable is a one-handed procedure to transport and screw the sealing caps into engagement. Thus a driving member, or screwdriver 27, is provided to matingly engage and retain the sealing caps and to carry the sealing caps to the housing opening 37.

The screwdriver 27 is a unitary, lightweight, plastic member, preferably of Delrin. An elongated handle portion 73 has a preferably hexagonal cross-section 74 for secure finger gripping, without slippage. Preferably, the handle portion 73 is approximately one and one-half to two inches in length.

Integral with the handle portion 73, at one end, is a blade portion 75. A protrusion 77 on the blade has a cross-sectional shape similar to that of the notch 55 on the sealing cap 23, but slightly larger in transverse dimension. That is, the thickness T of the protrusion is slightly greater than the notch width so that there is a compression or force-fit between the protrusion 77, and the notch 55. The protrusion 77, when force-fit into the notch 55, acts as a socket head.

When the protrusion 77 is inserted with a force-fit into the notch 55, the shape of the protrusion 77 is altered to fit within the notch 55. The protrusion 77 comprises a pair of resilient, rectangularly shaped members 79, parallel to each other and spaced slightly apart. The resilient members, or fingers, are defined by a slit 81 at the distal end of a rectangularly-shaped protrusion 77. The slit 81 effectively bisects the protrusion 77 into two fingers.

Transverse chamfers 83, parallel to the transverse direction of the slit 81, are provided as a camming, or biassing, surface which engages with the transverse edges 61 of the sealing cap 23. The interengagement between the edges 61 and the chamfer 83 serve to bias the members 79 in a direction toward the slit 81. The members 79 have a "memory of position", that is, they tend to retain their initial shape, and thus, when force-fit within the notch 55, bias outwardly against the lateral, or transverse, faces 59 of the notch 55, to thus retain the sealing cap 23 onto the screwdriver 27. Thus, the operator can, with one hand, insert the screwdriver 27 into engagement with the notch 55 to retain the sealing cap 23 thereto, and then position the cap 23 into engagement with the terminal block.

It should also be recognized that the screwdriver 27 and sealing cap 23 can be formed as a unitary combination. That is, the sealing cap 23 and the protrusion 77 can have a frangible connection (not shown) that connects the cap 23 to the screwdriver 27 before an initial use. After the cap 23 is secured within the housing 11, the screwdriver 27 can be pulled away from the sealing cap 23 to break the frangible connecion. For subsequent removal of the sealing cap 23, the sealing cap will be retained to the protrusion 77 in the manner as described above.

As previously discussed, it is essential that the set screws 17, 19, not be overtightened or overtorqued. Thus, a maximum torque wrench 21 is provided. The torque wrench 21, is of the Allen-type. The handle 85 is made of electrically insulating material, such as plastic, preferably Delrin. The handle 85 is hexagonally shaped for easy finger gripping without slippage.

Figure 6:
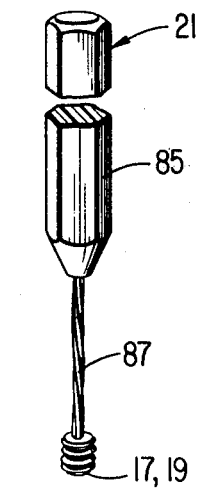
FIG. 6 is a perspective view of the maximum torque wrench after deformation.

The shaft 87 of the wrench 21 is hexagonally keyed at 88 to mate with the hexagonal socket head 51 of the set screw 17, 19. The shaft 87 is made of a particular material, having a particular length x extending from the handle, and of a particular cross-sectional shape such that it will yield and permanently twist or deform, as shown in FIG. 6, when a predetermined torque is reached. The operator will be able to observe the deformation and cease further rotation of the wrench.

One of ordinary skill in the art can design a wrench shaft 87 to yield at the predetermined torque level. In the preferred embodiment of the present invention, it is desired that the maximum torque of the set screw be approximately 8 inch-lbs. It has been found that the shaft 87 will deform at such a torque level when the shaft is made of steel, extends 0.75 inches from the handle ($x=0.75$), and has a hexagon-shaped cross-section compatible to mate with a hexagon-shaped set screw head measuring 0.050 inches across opposite flats.

It should be recognized that the maximum torque wrench after deformation, can still be employed to remove the set screw from the terminal block.

Above, specific embodiments of the present invention have been described. It should be appreciated, however, that these embodiments were described for purposes of illustration only, without any intention of limiting the scope of the present invention. Rather, it is the intention that the present invention be limited not by the above, but only as is defined in the appended claims.

What is claimed is:

1. In a medical device fully implantable in the body of a recipient having a casing hermetically sealed from the exterior environment surrounding the casing, electrical circuitry within said casing, a fluid-tight coupling mounted on said casing for interconnecting said electrical circuitry within said casing with an electrode lead implantable in the body of the recipient, said coupling including a housing made of electrically insulating material and defining a receptacle for an electrode lead, a terminal block contained within said housing and defining a lead opening for receiving an electrically conducting portion of the electrode lead, retaining means for retaining said conducting portion in the terminal block, a retaining means opening defined by said terminal block for accommodating said retaining means in said terminal block, a housing opening, defined by said housing, through which said retaining means can pass between the terminal block and the housing exterior, a sealing cap removably retained in said housing opening for preventing fluid communication between the housing exterior and the terminal block, and electrical conducting means for electrically interconnecting the terminal block with an electrical conductor exterior to the housing, the improvement comprising, said terminal block defining an externally-threaded boss extending within said housing opening, and said sealing cap comprising a threaded portion threadingly connected with said terminal block boss for removably retaining said sealing cap in said housing opening.

2. The implantable device of claim 1 wherein said retaining means opening defined by said terminal block extends through the terminal block boss and opens in said lead opening.

3. The implantable device of claim 2 wherein said terminal block boss and said retaining means opening are each extending substantially perpendicular to said lead opening.

4. The implantable device of claim 3 wherein said retaining means comprises a set screw, and wherein said retaining means opening is threaded for threadingly receiving said set screw, said set screw screwable within said retaining means opening into said lead opening for engaging and retaining said conducting portion of the electrode lead.

5. The implantable device of claim 4 wherein said set screw includes a socket head for receiving a wrench, and said coupling further includes a maximum torque wrench for engaging said socket head and torquing said socket head until a maximum predetermined torque is reached.

6. The implantable device of claim 5 wherein said wrench comprises a handle of electrically insulating material, and a shaft connected with said handle, said shaft having a keyed portion for engaging said socket head and rotating said set screw, said shaft yieldable at a predetermined maximum torque to prevent further rotation of said set screw.

7. The implantable device of claim 6 wherein said set screw is a hexagon socket head set screw measuring 0.050 inches across opposite flats, and wherein said wrench shaft is a metal shaft, hexagonally keyed for mating with said hexagon socket head set screw, having a length extending from said handle of approximately 0.75 inches.

8. The implantable device of claim 6 or 7 wherein said predetermined maximum torque is approximately 8 in-lbs.

9. The implantable device of claim 1 or 4 wherein said sealing cap comprises a head portion and a cylindrically shaped neck extending therefrom said neck internally threaded for threaded connection with said externally-threaded terminal block boss.

10. The implantable device of claim 9 wherein said neck defines an annular chamfer adjacent said head portion, said sealing cap further comprising an O-ring seal seated within said chamfer, said O-ring seal engaging said housing for preventing fluid communication between the housing exterior and the housing opening.

11. The implantable device of claim 10 wherein said housing opening includes a chamfered portion extending about said opening and engaging said O-ring seal when said sealing cap is in threaded connection with said terminal block boss.

12. The implantable device of claim 9 wherein said head portion includes a notch means for receiving a driving blade of a screwdriver.

13. The implantable device of claim 12 wherein said notch means is rectangularly shaped.

14. The implantable device of claim 13 wherein said screwdriver comprises a unitary, molded, plastic handle and driving blade, said driving blade adapted to be press-fit in said notch means so as to retain said sealing cap thereto.

15. The implantable device of claim 14 wherein the cross-sectional shape of said driving blade is substantially similar to said notch means shape, but slightly greater in dimension, said driving blade having a slit therewithin, wherein said driving blade is deformable to fit within said notch means.

16. The implantable device of claim 9 wherein said sealing cap is plastic.

* * * * *